United States Patent [19]
Steen et al.

[11] Patent Number: 5,377,823
[45] Date of Patent: Jan. 3, 1995

[54] COMPACT DENTAL DISPENSING TRAY WITH SLIDING COVER

[75] Inventors: Dirk L. Steen, Apple Valley; Malcolm W. Wilcox, Woodbury; Thomas W. Martin, Little Canada, all of Minn.

[73] Assignee: Minnesota Mining and Manufacturing Company, St. Paul, Minn.

[21] Appl. No.: 177,204

[22] Filed: Jan. 4, 1994

Related U.S. Application Data

[63] Continuation of Ser. No. 978,117, Nov. 18, 1992, abandoned.

[51] Int. Cl.⁶ .................. A01B 19/02; A61G 15/00
[52] U.S. Cl. .................... 206/63.5; 433/79
[58] Field of Search ........... 433/77, 79; 206/63.5, 206/447; 220/345, 349

[56] References Cited

U.S. PATENT DOCUMENTS

| D. 330,670 | 11/1992 | Georgakis et al. | D9/341 |
|---|---|---|---|
| 2,562,248 | 7/1951 | Weed | 220/345 |
| 2,975,889 | 3/1961 | Brown | 220/345 |
| 2,992,726 | 7/1961 | Simens | 220/345 |
| 3,630,344 | 12/1971 | Bergh et al. | 220/345 |
| 3,721,364 | 3/1973 | Lukaschewitz et al. | 220/345 |
| 3,756,387 | 9/1973 | Chaney | 220/345 |
| 4,333,567 | 6/1982 | Leonard | 206/368 |
| 4,473,156 | 9/1984 | Martin | 220/345 |
| 4,822,280 | 4/1989 | Rider | 206/63.5 |
| 4,978,007 | 12/1990 | Jacobs et al. | 206/368 |
| 4,991,759 | 2/1991 | Scharf | 224/217 |
| 5,106,297 | 4/1992 | Discko, Jr. | 433/77 |
| 5,122,057 | 6/1992 | Discko, Jr. | 433/90 |
| 5,139,188 | 8/1992 | Scharf | 224/217 |
| 5,249,963 | 10/1993 | McGarrigle | 433/163 |

FOREIGN PATENT DOCUMENTS 3435885 4/1986 Germany ................ 433/77

Primary Examiner—Gene Mancene
Assistant Examiner—Todd E. Manahan
Attorney, Agent, or Firm—Gary L. Griswold; Walter N. Kirn; James D. Christoff

[57] ABSTRACT

A dental dispensing tray has a plurality of wells formed in a substrate, along with a cover that is slidably attached to the substrate. The cover transmits at least a portion of the visible light spectrum but does not transmit a substantial portion of actinic radiation that might otherwise prematurely cure photocurable material in the wells.

8 Claims, 2 Drawing Sheets

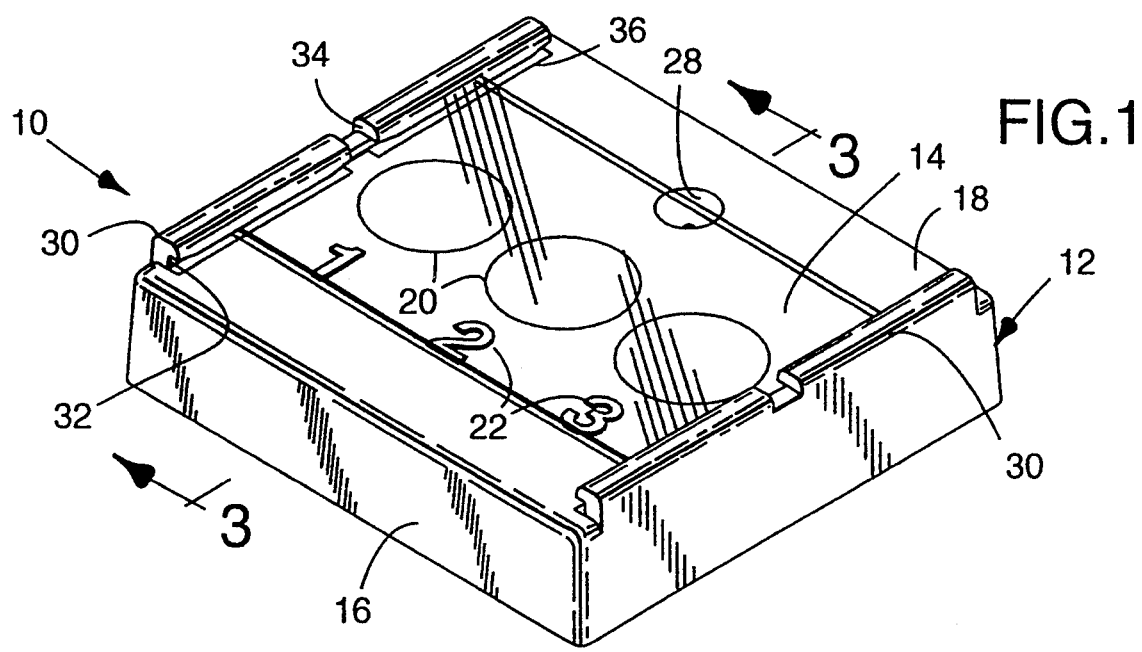
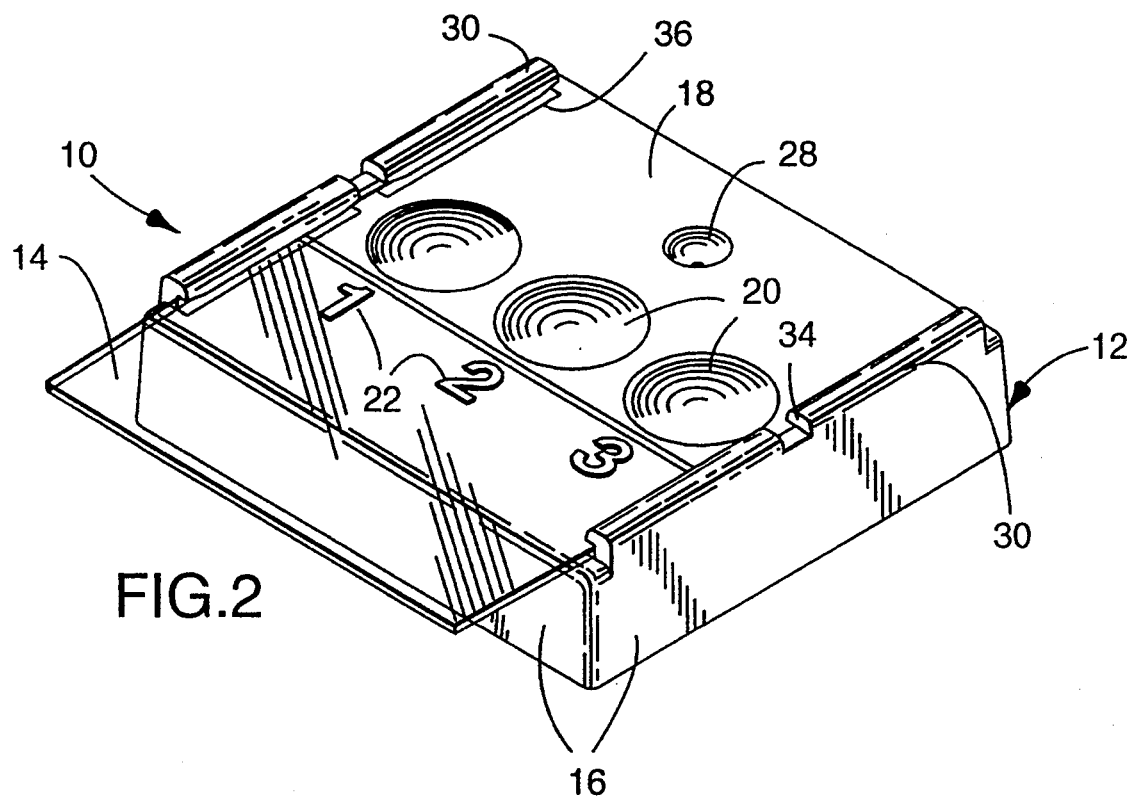

1

COMPACT DENTAL DISPENSING TRAY WITH SLIDING COVER

This is a continuation of application Ser. No. 07/978,117 filed Nov. 18, 1992 now abandoned.

BACKGROUND OF THE INVENTION

1. Field of the Invention

This invention relates to a tray for dispensing dental materials and is especially suitable for dispensing dental materials that are curable upon exposure to light.

2. Description of the Related Art

Photocurable dental materials have become increasingly popular in recent years. An example of light curable dental material includes the Scotchbond brand multi-purpose dental adhesive system available from the assignee of the present invention. The Scotchbond brand adhesive system includes an etchant for etching tooth enamel or dentin surfaces, a primer to facilitate wetting of the adhesive on the prepared tooth structure, and an adhesive that bonds to either etched enamel or dentin. Both the primer and the adhesive rapidly cure upon exposure to light in the visible spectrum.

A light curing unit is normally used to cure dental material. Such light curing units are hand-held by the user to enable the light to be directed into the oral cavity and toward the dental material when desired. Photocurable dental materials are advantageous because the material can be positioned exactly where desired and excess material can be removed before the light curing unit is activated to cure the material.

Photocurable dental materials are often sold in bulk in a dropper bottle, syringe or other container. Typically, a small quantity of the material is transferred from the container to a well of a dispensing tray adapted for use for a single patient, so that the likelihood of contamination of material in the bulk container is reduced. A brush or other tool is used to transfer material from the well to the tooth structure of the patient. The dispensing tray is then cleaned and sterilized before use for another patient.

It has been observed in the past that the background lighting of dental operatories is often sufficient to prematurely polymerize certain photocurable dental materials if left exposed for a sufficient amount of time. To avoid such an occurrence, the dispensing tray may be temporarily covered with an opaque sheet to prevent at least some of the visible light from reaching dental material in wells of the tray. Alternatively, a dispensing tray with an opaque cover can be used, such as the dispensing tray with a hinged cover that is described in U.S. Pat. No. 5,139,188. A dispensing tray having an opaque sliding cover is described in U.S. Pat. No. 4,822,280.

Some photocurable dental materials have a relatively low viscosity and thus may easily overflow from the well of the dispensing tray if the tray is unduly tilted or jostled during use. Unfortunately, such an event may cause the material to be spilled onto the floor or otherwise wasted, or enter an adjoining well where it may undesirably mix with another dental material.

OTHER ART

A package containing an orthodontic bracket that is precoated with a photocurable adhesive is described in U.S. Pat. No. 4,978,007, assigned to the assignee of the present invention. The package has a substrate with a well for holding the precoated bracket, and has a cover which transmits at least part of the visible light spectrum and does not transmit a substantial portion of actinic radiation. In one embodiment, the bottom of each well is coated with a release-coating material for contact with the adhesive, while in another embodiment each well has a pair of grooves for suspending the bracket by its long axis indicator. It is mentioned in U.S. Pat. No. 4,978,007 that the cover of the package may be a rigid sheet that is attached to the tray by cooperating tongue-and-groove appendages that permit the plate to slide relative to the substrate.

SUMMARY OF THE INVENTION

The present invention concerns in one embodiment a dispensing tray for dental material and comprises a substrate having at least one well for containing a quantity of dental material curable by exposure to actinic radiation. The tray includes a cover that transmits at least part of the visible light spectrum and does not transmit a substantial portion of the actinic radiation. A means is provided for slidably coupling the cover to the substrate in order to enable the cover to move from a first orientation covering the well to a second orientation at least partially uncovering the well. The cover when in the second orientation projects past the substrate.

Another embodiment of the present invention concerns a dispensing tray for dental material and comprises a substrate having at least one well for containing a quantity of dental material curable by exposure to actinic radiation. The tray includes a cover that transmits at least part of the visible light spectrum and does not transmit a substantial portion of the actinic radiation. A means is provided for slidably coupling the cover to the substrate in order to enable the cover to move from a first orientation covering the well to a second orientation at least partially covering the well. The substrate has overall dimensions sufficiently small to enable the substrate to entirely fit within the confines of a human hand.

In both embodiments, the cover enables the user to observe whether or not dental material is present in the well without opening the cover. The cover also prevents sufficient light from entering the well when the cover is closed so that dental material in the well does not unduly cure. The means for slidably coupling the cover to the substrate allows the user to open the cover in smooth fashion, with reduced likelihood of tilting or jostling the tray so that spillage of material from the well is largely avoided.

BRIEF DESCRIPTION OF THE DRAWINGS

FIG. 1 is a perspective view of a dispensing tray in accordance with the invention;

FIG. 2 is a perspective view somewhat similar to FIG. 1 except that a cover of the tray is shown in an open orientation.

DETAILED DESCRIPTION OF THE PREFERRED EMBODIMENT

Figure 3:
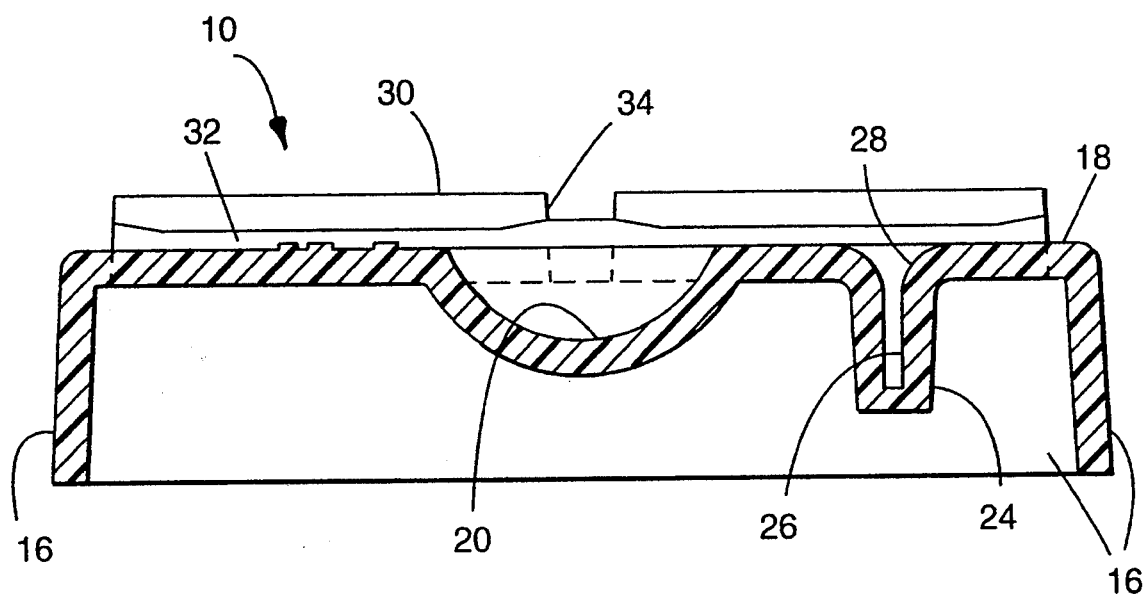
FIG. 3 is an enlarged cross-sectional view of the tray shown in FIGS. 1-2 taken along lines 3—3 of FIG. 1, except that the cover has been removed.

A dispensing tray 10 is illustrated in FIGS. 1-3 and includes a base substrate 12 and a cover 14 (FIGS. 1-2 only). The substrate 12 includes four upright walls 16 that are integrally connected at their upper edges to a horizontally-extending platform 18 having an overall rectangular shape.

The platform 18 is connected to three side-by-side mixing wells 20 aligned along a central axis of the platform 18 in its elongated direction. The mixing wells 20 have a smoothly curved configuration similar to a partial sphere and unbroken by recesses, grooves and the like, and are adapted to contain a quantity of dental material that is curable upon exposure to actinic radiation. As can be observed in FIG. 1, the wells 20 are identified by numerical indicia 22 to assist the user in remembering which type of material is in a particular well 20.

A depending, somewhat cylindrical body 24 (FIG. 3) is integrally connected to the platform 18, and includes an elongated vertical passage 26 that is essentially cylindrical, but preferably has a slight frustoconical taper in the range of 1 to 2 degrees to facilitate molding. A trumpeted or chamfered entrance 28 is connected to the passage 26, and as shown in FIG. 3 provides a smoothly curved transition between the passage 26 and a top of the platform 18. The arc forming the entrance 28 is tangential at its uppermost end with the top of the platform 18, and is tangential at its lowermost end with the inner wall of the body 24 defining the passage 26.

Preferably, the passage 26 has a diameter in the range of 0.8 mm to 0.9 mm, and the radius forming the entrance 28 is 2.3 mm. The lower end of the passage 26 is spaced from the top of the platform 18 a distance of 6.3 mm to limit insertion of the syringe tip. The passage 26 together with the entrance 28 is useful for bending the tip of a dispensing syringe, and further information may be obtained by referring to co-pending U.S. patent application Ser. No. 07/977,926 filed on even date herewith.

A pair of elongated, upstanding bars 30 are integrally connected to the platform 18 along the shorter two of the four walls 16. The bars 30 include inwardly directed flanges that present opposed grooves 32. Each of the bars 30 has a central, upper notch 34 that extends through the respective flanges. As shown for example in FIG. 3, the flanges have a tapered lead-in next to the grooves 32 along their outer ends as well as in areas adjacent the notches 34.

The cover 14 has an overall rectangular configuration with slightly rounded corners, and the shorter pair of edges of the cover 14 are received in the grooves 32 for sliding movement therealong. The thickness of the cover 14 is 0.76 mm, while the height of the grooves 32 is 0.86 mm in order to facilitate sliding of the cover 14 in smooth fashion. Rectangular cutouts 36 in the platform 18 are disposed below overhanging portions of the flanges of the bars 30 as illustrated in FIG. 1.

The overall dimensions of the substrate 12 are sufficiently small (for example, 5.2 cm×4.8 cm×1.3 cm) such that the entire substrate 12 comfortably fits within the confines of one hand. The underside of the substrate 12 is open, and the bottom of the wells 20 and the inner surfaces of the walls 16 provide finger-gripping structure for the fingers of one hand to hold and also to steady movement of the tray 10 while the thumb of the same hand is placed atop the cover 14 for manipulating movement of the cover 14 relative to the substrate 12. If desired, ridges, recesses or other types of frictional thumb-engaging structure may be provided on the top of the cover 14 to enhance engagement of the thumb with the cover 14 during sliding motion.

The grooves 32 together with the notches 34 provide structure for enhancing smooth sliding motion of the cover 14 relative to the substrate 12, so that dental materials such as liquids having a relatively low viscosity are not spilled or otherwise dislodged from the wells 20 as the cover 14 is moved from its first, closed orientation that is illustrated in FIG. 1 and to a second, open orientation that is illustrated in FIG. 2. The second orientation is spaced from the first orientation a sufficient distance to uncover the wells 20. The notches 34 provide stress relief for the bars 30 when the walls 16 are inadvertently squeezed together, so that the bars 30 do not unduly bind against the edges of the cover 14 and hinder movement of the latter.

The substrate 12 and the bars 30 are integrally molded of black polypropylene that is opaque to light in the visible spectrum including actinic radiation that might otherwise prematurely cure material in the wells 20. On the other hand, the cover 14 is made from a sheet of poly(ethylene glycol-co-cyclohexane-1,4-dimethanol terephthalate) (PETG) that includes sufficient colorant (preferably, an orange colorant) to prevent transmission of a substantial portion of actinic radiation, and yet transmit at least part of the visible light spectrum so that dental material in the wells 20 can be observed when the cover 14 is in its closed position. Other suitable materials for the cover 14 are described in U.S. Pat. No. 4,978,007, the disclosure of which is incorporated by reference herein.

The bars 30, including the grooves 32, comprise a means for slidably coupling the cover 14 to the substrate 12 in order to enable the cover to smoothly move between an open and a closed orientation. Importantly, the tray 10 lacks any snap-action latch such as molded dimples, recesses or protrusions for releasably retaining the cover 14 in a closed or an open position, as such structure might otherwise cause the tray 10 to be sufficiently jolted during movement of the cover 14 to cause material in the wells 20 to be spilled or otherwise dislodged. The thickness of the cover 14 is sufficiently large to preclude the cover 14 from freely falling from the grooves 32 when the tray 10 is tilted.

The width of the cover 14 (i.e., the shorter of the two dimensions along the plane of the cover 14) relative to the width of the substrate 12 is sufficiently small to enable a portion of the cover 14 to project past the adjacent upright wall 16 of the substrate 12 when the cover 14 is moved to its open position as shown in FIG. 2. The projecting cover 14 when open is easy to engage by the fingers of the same hand that is holding the tray, so that return movement of the cover 14 to its closed position is facilitated.

We claim:
1. A dispensing tray for dental material comprising:
a substrate having at least one well for containing a quantity of dental material curable by exposure to actinic radiation;
a cover that transmits at least part of the visible light spectrum and does not transmit a substantial portion of the actinic radiation; and
means for slidably coupling said cover to said substrate in order to enable said cover to move from a first orientation covering said at least one well to a second orientation at least partially uncovering said at least one well, said cover when in said second orientation projecting past said substrate, wherein said means for slidably coupling said cover to said substrate comprises a pair of upstand- ing, elongated bars connected to said substrate, said bars presenting opposed grooves for contact with said cover, and wherein said bars have relief notches for enhancing sliding movement of said cover.

2. The tray of claim 1, wherein said means for slidably coupling said cover to said substrate includes means for enabling smooth movement of said cover from said first orientation to said second orientation using only one hand while said hand is also providing sole support for said substrate.

3. The tray of claim 1, wherein said means for slidably coupling said cover to said substrate is substantially free of detents or projections in order to enable said cover to smoothly move from said first orientation to said second orientation.

4. The tray of claim 1, wherein said substrate is opaque to both visible light radiation and actinic radiation.

5. The tray of claim 1 including means substantially precluding said cover from falling from said substrate when said tray is tilted.

6. The tray of claim 5, wherein said means for slidably coupling said cover to said substrate includes a pair of opposed grooves for receiving said cover, wherein said cover has a certain thickness, and wherein said means substantially precluding said cover form falling from said substrate when said tray is tilted comprises said certain thickness of said cover.

7. A dispensing tray for dental material comprising:
   a substrate having at least one well for containing a quantity of dental material curable by exposure to actinic radiation;
   a cover that transmits at least part of the visible light spectrum and does not transmit a substantial portion of the actinic radiation; and
   means for slidably coupling said cover to said substrate in order to enable said cover to move from a first orientation covering said at least one well to a second orientation at least partially uncovering said at least one well, said substrate having overall dimensions sufficiently small to enable said substrate to entirely fit within the confines of a human hand, wherein said means for slidably coupling said cover to said substrate comprises a pair of upstanding, elongated bars connected to said substrate, said bars presenting opposed grooves for contact with said cover, and wherein said bars have relief notches for enhancing sliding movement of said cover.

8. The tray of claim 7, wherein said means for slidably coupling said cover to said substrate is substantially free of detents or projections in order to enable said cover to smoothly move from said first orientation to said second orientation.

* * * * *